(12) United States Patent
Marterstock et al.

(10) Patent No.: US 12,329,888 B2
(45) Date of Patent: Jun. 17, 2025

(54) APPARATUS AND METHOD FOR PREPARING DIALYZATE

(71) Applicant: FRESENIUS MEDICAL CARE DEUTSCHLAND GMBH, Bad Homburg (DE)

(72) Inventors: Stefan Konrad Marterstock, Dettelbach (DE); Torsten Keller, St. Wendel (DE); Benedict Glaser, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 497 days.

(21) Appl. No.: 17/795,259

(22) PCT Filed: Jan. 26, 2021

(86) PCT No.: PCT/EP2021/051722
§ 371 (c)(1),
(2) Date: Jul. 26, 2022

(87) PCT Pub. No.: WO2021/151874
PCT Pub. Date: Aug. 5, 2021

(65) Prior Publication Data
US 2023/0146806 A1    May 11, 2023

(30) Foreign Application Priority Data

Jan. 28, 2020  (DE) .................... 10 2020 101 969.6
Mar. 12, 2020  (DE) .................... 10 2020 106 749.6
Mar. 12, 2020  (DE) .................... 10 2020 106 751.8

(51) Int. Cl.
*A61M 1/16*    (2006.01)
*A61M 1/14*    (2006.01)
(Continued)

(52) U.S. Cl.
CPC .......... *A61M 1/1672* (2014.02); *A61M 1/154* (2022.05); *A61M 1/166* (2014.02);
(Continued)

(58) Field of Classification Search
CPC .... A61M 1/1672; A61M 1/154; A61M 1/166; A61M 1/287; B01D 61/0022;
(Continued)

(56) References Cited

U.S. PATENT DOCUMENTS

2015/0144553 A1\*  5/2015  Vogel ................... B01D 71/56
                                                        521/53
2015/0209500 A1    7/2015  Lin et al.
(Continued)

FOREIGN PATENT DOCUMENTS

DE    10 2017 118 718 B3    6/2018
DE    10 2018 118 564 A1    2/2020
(Continued)

OTHER PUBLICATIONS https://aquaporin.com/what-is-forward-osmosis/ (Year: 2025).\*
(Continued)

*Primary Examiner* — Chester T Barry
(74) *Attorney, Agent, or Firm* — Kilyk & Bowersox, P.L.L.C.

(57) ABSTRACT

The present invention relates to an apparatus and a method for preparing dialyzate, wherein the apparatus has a first part and a second part that is configured as a circuit; wherein the first part comprises a water connection or a water container as well as the primary side of a filter; wherein the filter is configured to prepare purified water from the water through forward osmosis; and wherein the second part comprises the secondary side of the filter, a reservoir, a filtrate line that leads from the secondary side of the filter to the reservoir, and a line leading from the reservoir to the secondary side (Continued)

Figure 1:
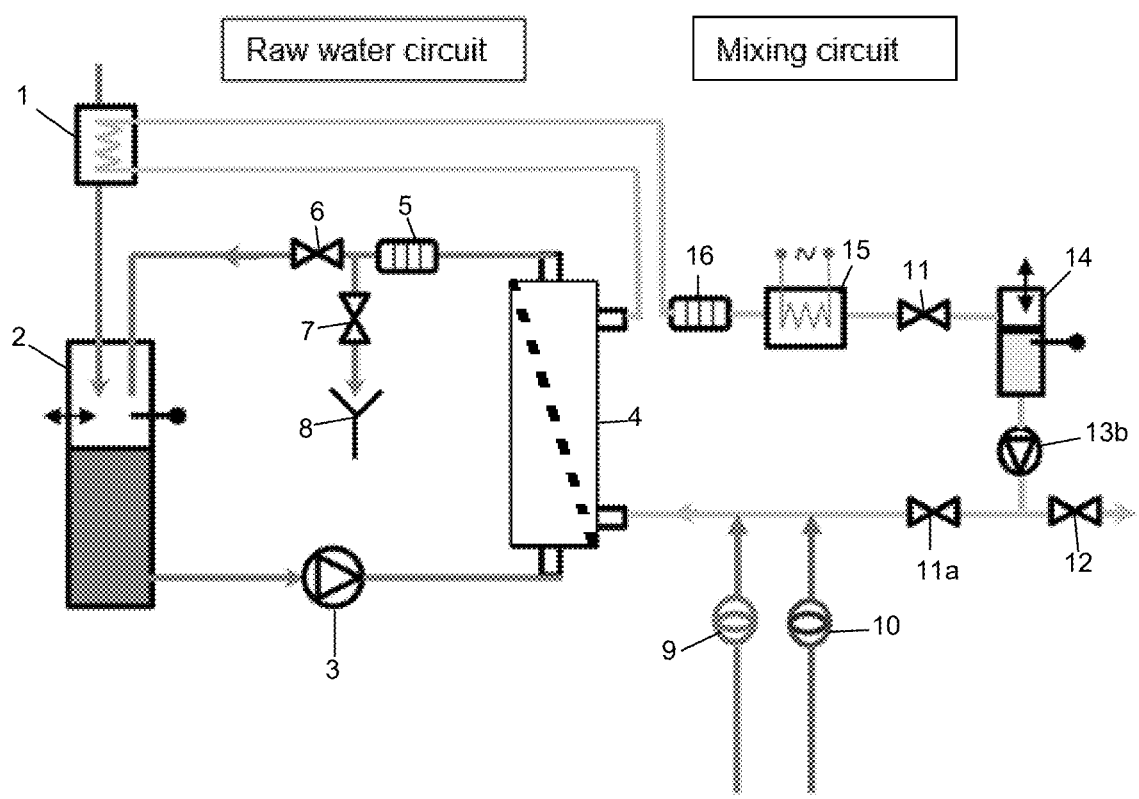

of the filter, with the reservoir being a container having means for connecting the container to a dialysis machine.

16 Claims, 3 Drawing Sheets

(51) Int. Cl.
| | |
|---|---|
| *A61M 1/28* | (2006.01) |
| *B01D 61/00* | (2006.01) |
| *B01D 61/46* | (2006.01) |
| *B01D 61/54* | (2006.01) |
| *B01D 61/58* | (2006.01) |
| *C02F 1/44* | (2023.01) |
| *C02F 1/469* | (2023.01) |
| *C02F 103/02* | (2006.01) |

(52) U.S. Cl.
CPC ......... *A61M 1/287* (2013.01); *B01D 61/0022* (2022.08); *B01D 61/0024* (2022.08); *B01D 61/005* (2013.01); *B01D 61/46* (2013.01); *B01D 61/54* (2013.01); *B01D 61/58* (2013.01); *C02F 1/445* (2013.01); *C02F 1/4693* (2013.01); *A61M 2205/3327* (2013.01); *B01D 2311/08* (2013.01); *B01D 2313/221* (2022.08); *B01D 2313/243* (2013.01); *B01D 2313/28* (2013.01); *B01D 2313/30* (2013.01); *B01D 2313/60* (2022.08); *B01D 2317/022* (2013.01); *B01D 2317/08* (2013.01); *C02F 2103/026* (2013.01); *C02F 2209/05* (2013.01); *C02F 2305/08* (2013.01)

(58) Field of Classification Search
CPC .. B01D 61/0024; B01D 61/005; B01D 61/46; B01D 61/54; B01D 61/58; C02F 1/445; C02F 1/4693
See application file for complete search history.

(56) References Cited

U.S. PATENT DOCUMENTS

2016/0016127 A1* 1/2016 Mentzel ............... A01C 23/042
                                                              210/257.2
2021/0276889 A1* 9/2021 Chladek .................. C02F 1/44

FOREIGN PATENT DOCUMENTS

| EP | 3 187 211 A1 | 7/2017 |
|---|---|---|
| EP | 3 272 375 A1 | 1/2018 |
| WO | WO 2009/083011 A2 | 7/2009 |
| WO | WO 2014/121168 A1 | 8/2014 |
| WO | WO 2014/128293 A1 | 8/2014 |
| WO | WO 2015/124716 A1 | 8/2015 |

OTHER PUBLICATIONS

J. Pittard, "Safety Monitors in Hemodialysis" in chapter 13 of Handbook of Dialysis Therapy (5th edition) (editors Nissenson and Fine; publisher: Elsevier, 2017) (the portion relied upon appears at p. 10 of Office action) (Year: 2017).*

Smith, M.C. et al., Forward osmosis dialysate production using spiral-wound reverse-osmosis membrane elements. In: Journal of Membrane Science, 469, 2014, pp. 95-111.

* cited by examiner

APPARATUS AND METHOD FOR PREPARING DIALYZATE

The present invention relates to an apparatus and to a method for preparing dialyzate.

It is known from the prior art to supply dialysis machines with a ready-to-use dialyzate from, e.g. a line system that is connected to a central device for preparing the dialyzate and that is generally configured to supply a plurality of dialysis machines with dialyzate.

It is further known from the prior art to prepare the dialyzate at the dialysis machine itself, i.e. decentrally. An RO system (RO=reverse osmosis) that is part of the dialysis machine or that can be designed as a separate unit can be provided for this purpose for the preparation of ultrapure water. The ultrapure water is mixed with one or more concentrates in the dialysis machine to obtain a ready-to-use dialyzate for the treatment of the patient. There is a disadvantage in the preparation of ultrapure water by means of the RO process in that the process requires high pressures in the range from 6 to 15 bar, which is correspondingly energy-intensive.

It is the underlying object of the present invention to provide an apparatus and a method by means of which an energy-efficient dialyzate preparation is possible.

This object is solved by an apparatus having the features of claim 1 and by a method having the features of claim 12.

Provision is accordingly made that the apparatus has a first part and a second part that is configured as a circuit, wherein the first part comprises a water connection or a water container as well as the primary side of a filter, wherein the filter is configured to prepare purified water from the water through forward osmosis, and wherein the second part comprises the secondary side of the filter, a reservoir, a filtrate line that leads from the secondary side of the filter to the reservoir, and a line leading from the reservoir to the secondary side of the filter, with the container having means for connecting the container to a dialysis machine.

Provision is preferably made that raw water or tap water is drawn from the water container or from the water connection.

One or more concentrates from which a dialyzate can be prepared by dilution or solution in the permeate can be located in the container.

The term "dialyzate" within the framework of the present invention comprises both a ready-to-use dialysis solution and one or more components thereof.

It is thus the underlying idea of the present invention to utilize the different electrolyte concentration between the raw water and the dialyzate/concentrate and the osmotic pressure associated therewith to prepare dialyzate with the aid of a suitable forward osmosis membrane of the filter. The forward osmosis is also abbreviated to FO in the following.

For the preparation of dialyzate, the permeate is mixed with one or more concentrates after preparation until a physiological electrolyte concentration or the desired electrolyte concentration is reached. At least one of the concentrates is preferably located in the reservoir. It is conceivable that at least one concentrate (or all the concentrates) is (or are) supplied to the second part of the apparatus via a concentrate line.

The substance concentration of electrolytes (and thus the conductivity as a sum parameter for the electrolyte concentration) is considerably higher in the dialyzate or in the dialysis concentrate than in tap water. The electrical conductivity of drinking water (according to the German Drinking Water Ordinance) thus amounts to a maximum of 2.79 mS/cm; the electrical conductivity of dialyzate to typically 12 to 16 mS/cm. This difference (that does not restrict the invention) in the electrolyte concentration results in an osmotic pressure gradient that is utilized in accordance with the invention for the process of the dialyzate preparation by FO.

The water, which is preferably tap water, is heated (preferably to 37° C.) for the preparation of dialyzate or dialyzate concentrate. If this is done directly at the start of the process, the efficiency of the FO process is improved since the osmotic pressure gradient is directly temperature dependent.

A substantial element of the invention is the use of forward osmosis for dialyzate preparation. It is not the use of used dialyzate that is the primary aim here, but rather the preparation of raw water, e.g. from the domestic supply. The FO membrane is thus preferably also a sterile barrier so that a good home dialysis is possible from concentrates (dry, liquid, etc.) both for HD (hemodialysis) and for PD (peritoneal dialysis).

The concentrate or the dialyzate is preferably conducted in the circuit for so long until the desired end concentration, end conductivity, etc. has been reached.

The second part of the apparatus is a circuit. In a preferred embodiment of the invention, the first part of the apparatus is also configured as a circuit, i.e. the water is led past the primary side of the filter in the circuit and the dialyzate or the dialysis concentrate is led past the secondary side of the filter in the circuit.

One, or better two, small chamber(s) or container(s) can, for example, be filled with ready-to-use dialyzate using an apparatus in accordance with the present invention, so that there is always a chamber available for the removal of dialyzate. This apparatus is also called a "microbatch" within the framework of this invention. Provision can, however, also be made to lay in a large store of, for example, 2-5 l (typical for PD) or 70-100 l (typical for HD) in a container, in particular a bag, for example. Such an apparatus or method is also called a "macrobatch" within the framework of this invention.

An FO process utilizes the osmotic pressure gradient for the filtration of water, preferably of tap water. The energy-intensive production of permeate by RO does not take place in accordance with the invention and dialyzate or dialyzate concentrate is prepared directly. Since the treatment process preferably takes place directly before the use of the fluid, i.e. there is no pipeline network present therebetween, the effort to maintain the required hygiene is simplified. In addition, new possibilities with respect to portability are conceivable due to continuing miniaturization. The process is additionally considerably quieter than that of an RO system having an associated pump for the pressure generation.

The container preferably is a bag that has flexible walls in part or overall. A container that has rigid walls in part or overall such as a cartridge is also conceivable and covered by the invention.

It is preferred that a plurality of containers, preferably two, are provided and that a valve arrangement is present that is configured to alternatingly switch in the containers to the second circuit. The container respectively not connected into the second circuit can be removed and employed for use in the dialysis. At the same time, the other container is filled with the ready-to-use dialyzate or with dialyzate concentrate.

Said means of the container can be a connector or a tube or a connector for a tube or other means by which fluid communication can be established between the interior of the container and a dialysis machine. The container, that is preferably configured as a bag, is preferably directly fixable to a dialysis machine by a counter-piece by means of a connector. It is also conceivable that the container has a tube or an adapter for a tube by means of which the ready-to-use dialyzate or dialysis concentrate can be used such as in the field of peritoneal dialysis.

The concentrate preferably present in the container can, for example, be a bicarbonate concentrate and/or an acid concentrate that is formed for the preparation of dialyzate.

The concentrate can be present in the container e.g. as a powder, granulate, slurry, or in liquid form.

A pump is preferably arranged in the first part and/or in the second part of the apparatus that is also called a "second circuit". If the pump is in the first part, a sufficiently high pressure can be generated on the primary side of the filter by means of the pump. The pump on the secondary side has the advantage that the dialyzate or the dialysis concentrate can be repeatedly led past the filter membrane so often until the desired concentration or conductivity, etc. has been reached.

A sensor, preferably a conductivity measuring cell, can be arranged in the second circuit to detect the end point in time of the preparation of the dialyzate or of the dialyzate concentrate. If said conductivity measuring cell has a measurement value that is within a desired value range, the preparation of the dialyzate or of the dialyzate concentrate can be considered ended and the container can be removed for use in the dialysis treatment.

It is conceivable that a concentrate line that is in turn connected to a reservoir for dialysis concentrate opens into the second circuit so that a further concentrate can be introduced into the second circuit by means of the concentrate line. This is sensible for the case that all the required concentrates are not present in the container, but only some of them.

The container can have exactly one compartment in which one or more concentrates are present that are dissolved by means of the permeate within the framework of the present invention. It is also conceivable that the container has a plurality of compartments in which one or more concentrates are respectively present. It is possible in this context that the compartments are arranged and configured such that they open in a time staggered manner so that specific osmolarities are present in a time staggered manner.

The present invention further relates to a method of manufacturing a dialyzate using an apparatus in accordance with one of the claims 1 to 12, wherein water, preferably tap water, is supplied to the primary side of the filter, wherein the permeate is supplied to the secondary side by forward osmosis, and wherein a dialyzate or a dialysis concentrate that is mixed with the permeate is supplied to the secondary side of the filter from the container and/or from another source.

Provision is preferably made that the dialyzate or the dialysis concentrate is conveyed in the circuit on the secondary side until the conductivity and/or a concentration or another parameter correlated therewith corresponds to a desired value or is in a desired value range.

It is conceivable that in the case of the presence of a plurality of containers, one container is filled with the dialyzate or with the dialysis concentrate in the second circuit and the other container is emptied for use in a dialysis machine, i.e. as part of a dialysis treatment.

It is advantageous for a physiologically compatible substance, in particular glucose, or a substance to be deposited prior to the use as a dialysis solution, in particular magnetic nanoparticles, to be admitted to increase the osmotic pressure on the secondary side.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment shown in the drawing.

Figure 2:
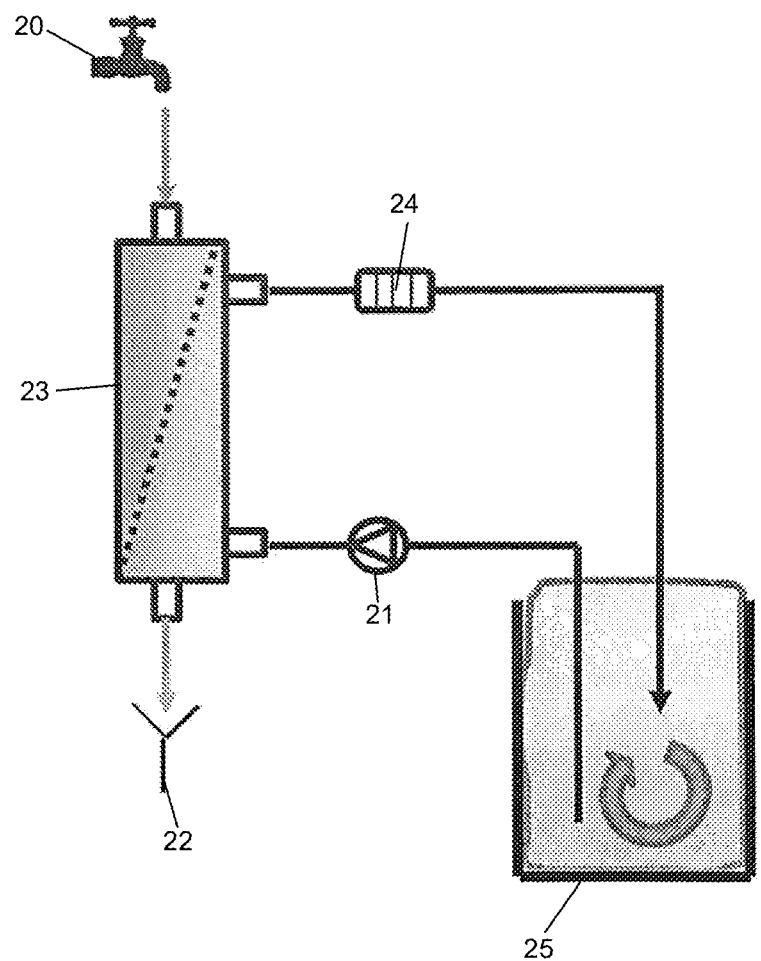
Figure 3:
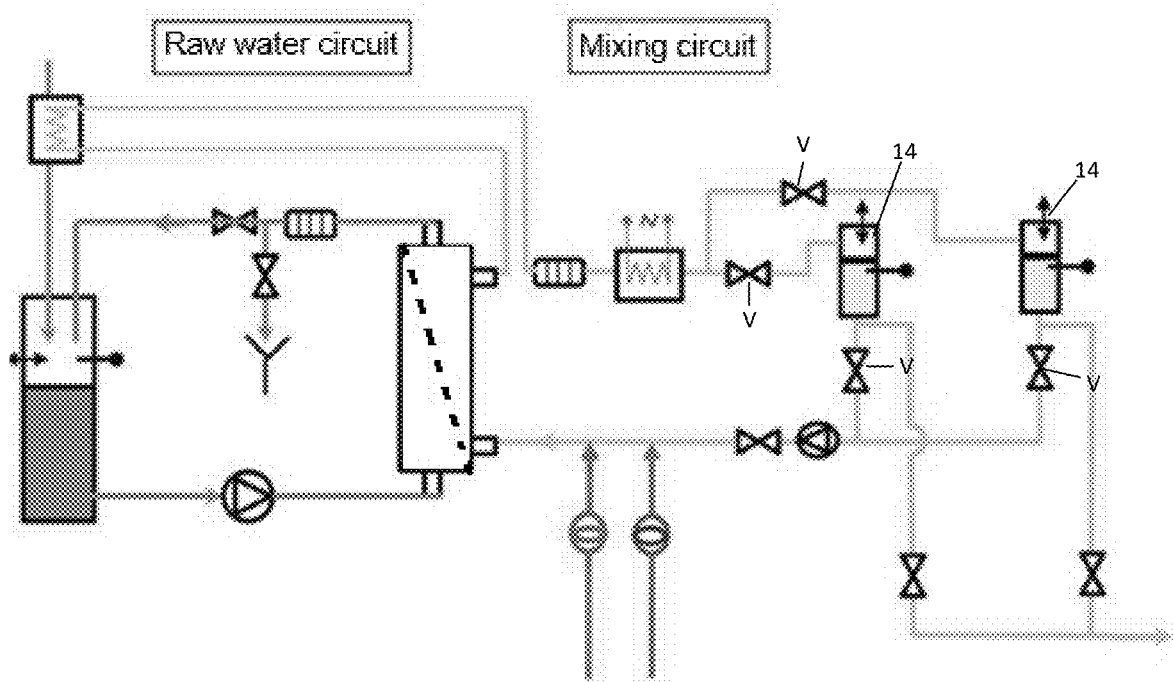

There are shown:

FIG. 1: a schematic flowchart of an apparatus in accordance with the invention in a first embodiment (microbatch);

FIG. 2: a schematic flowchart of an apparatus in accordance with the invention in a second embodiment (macrobatch); and FIG. 3: a schematic flowchart of an apparatus in accordance with the invention in a third embodiment (2× microbatch).

FIG. 1 shows a heat exchanger at the raw water inflow by reference numeral 1. The heating of the raw water supplied to the filter 4 increases the effectiveness of the osmosis process. The raw water inlet chamber that has a ventilation and/or a level sensor is marked by reference numeral 2.

As can be seen from FIG. 1, the apparatus comprises a first part in the form of the raw water circuit and a second part in the form of the mixing circuit.

Reference numeral 3 designates the circulation pump in the raw water circuit, i.e. in the circuit that is first in accordance with the invention. The FO filter is marked by 4 and 5 designates the conductivity-temperature measuring cell for raw water and backflow monitoring. Reference numeral 6 designates the raw water circulation valve and 7 the flush valve to flush the filter 4.

8 marks the drain and 9 an A concentrate pump (dialysis concentrate/acid concentrate) (A concentrate can also be added later) and 10 a B concentrate pump (dialysis concentrate/bicarbonate concentrate).

Reference numeral 11 designates a mixing circuit circulation valve and 11a a shut-off valve that is controlled by means of a control unit so that it closes as soon as the target conductivity has been reached.

Reference numeral 12 is the dialyzate removal valve and 13b is the circulation pump in the mixing circuit, i.e. in the circuit that is second in accordance with the invention.

Reference numeral 14 designates a concentrate bag that serves as a collection chamber and can be designed with ventilation and with a level sensor (the filtrate is accumulated here). Two parallel collection chambers, preferably concentrate bags, are preferably provided, as can be seen from FIG. 3. One chamber can thus always be filled with dialyzate and the respective other chamber can always be emptied or used as part of the dialysis treatment.

Reference numeral 15 is a heating that can also be arranged at the position of the heat exchanger, reference numeral 16 is a conductivity-temperature measuring cell for monitoring the dialyzate quality and composition (filtrate+bicarbonate mixing ratio or filtrate+bicarbonate+acid concentrate mixing ratio). Alternatively, a second measuring cell can be used for readjusting the B concentrate.

The routine for preparing dialyzate or dialysis concentrate runs as follows by way of example:

0. Initial Preparation

The FO filter 4 at the raw water side, i.e. at the side of the first circuit, is filled with raw water (tap water).

The FO filter 4 is filled with a physiological solution or with raw water at the filtrate side or permeate (=filtrate) is pressed toward the filtrate side by a small excess pressure on the raw water side.

1. Concentration Addition to the Mixing Circuit

Example: Volume in the mixing circuit: 800 ml (400 ml in the filter/400 ml in the circuit) Addition of concentrate: 11.4 ml A concentrate and 14 ml B concentrate.

2. Permeate Addition in the Mixing Circuit

Permeate (filtrate) is refilled through the FO membrane until the correct mixing ratio has been established. This is relevant to the osmotic pressure and thus to the permeate flow through the membrane.

Monitoring of the mixing ratio (target Na concentration in the dialyzate typically 138 mmol/L) by measuring the dialyzate conductivity (typically 12 to 16 mS/cm).

3. Removal of the Completed Dialyzate

New cycle starts with the addition of concentrate (1→2→3) The total process can also be configured as a continuous process with continuous concentrate addition, permeate production, and dialyzate removal.

It is additionally possible to install a second collection chamber or collection container and preferably a bag that is filled alternatingly with the first chamber. A dialyzate removal can thus take place from one chamber while the other chamber is being filled. A quasi-continuous dialyzate production is thus ensured.

Options for increasing the osmolarity at the product side of the filter 4 can preferably be named as:

To increase the osmotic gradient between tap water and dialyzate and thus the performance of the osmosis process, it is possible on the product side, i.e. in the second circuit:

a. To add a physiologically compatible additive. Glucose would be a possible substance here that is already present today in concentrations up to 1 g/l in HD dialyzate.

b. To add a substance that does not remain in the dialyzate, but is rather physically or chemically separated beforehand (or is retained by the dialyzer). Magnetic iron nanoparticles would be suitable for this. The particles are added upstream of the filter and are separated after the filter with the aid of a magnetic field.

A return of the consumed dialyzate to chamber 2 would also be conceivable to carry out a re-treatment and thus to save energy and water.

It is likewise conceivable to support the FO process in filter 4 by an additional, hydraulic pressure or by vacuum of a pump.

The following can be named as a supplementary idea: To test the forward osmosis filter 4 in operation to ensure that the retention function is still ensured.

It becomes necessary on the use of the forward osmosis technique in sensitive areas such as dialysis technology to ensure or at least monitor the correct functioning of the FO membrane.

There can be named as possible solutions:

1. Measuring the osmotic pressure adopted on a correct function of the FO membrane. If the membrane is in order, a transmembrane pressure is built up over the FO membrane (the osmotic pressure). The inlets and outlets of the FO filter can be blocked by valves and the osmotic pressure can be measured using a pressure sensor. The filter is correspondingly filled beforehand (with concentrate on the secondary side and with e.g. tap water on the primary side). The pressure adopted then has to remain constant over a certain time period; it must otherwise be assumed that a direct mixing of the fluids normally separated by the FO membrane takes place.

2. Priming the FO filter by pressing tap water on the permeate side and subsequently measuring the conductivity of the permeate.

3. Determining the fluid amounts that have flowed in and that have been removed (at the FO filter) and their conductivity. A validation of the dilution by the FO process can then be carried out using the values.

4. Fill the filter with air on the secondary side. Apply fluid to the primary side and measure the pressure from which the filter is penetrated, i.e. fluid passes over to the secondary side (the so-called bubble point test).

After the macrobatch preparation, the dialyzate production assisted by forward osmosis takes place as follows:

The solution is prepared in one or more batches. The batch can e.g. be a bag that includes the concentrates for preparing the solution in solid or liquid form. It is advantageous if the amount of dialyzate is sufficient to carry out one dialysis treatment (60 L to 250 L).

A description of a possible embodiment of the method is as follows:

Primary Side

The primary side (feed side) of the FO membrane is connected to a raw water source (tap water connection). The pressure of the raw water sources or a separate pressure increasing device (pump or hydraulic accumulator) ensures that the primary side is flowed over by raw water. The same pressure source can also be used to initially fill the primary side.

Secondary Side/Secondary Circuit

The secondary side ("product" side) of the FO membrane is connected to the batch, i.e. to the container, preferably to the bag. A separate pressure increasing device (pump or hydraulic accumulator) ensures that the secondary side is flowed over by solution.

The solution is preferably repeatedly led along the FO membrane. I.e. the batch is connected to the FO filter via a circuit.

Priming (Filling)

Initially, only the concentrates are present in dry form or in a slight dilution in the batch (as a powder, granulate, slurry, or in liquid form). The concentrates are dissolved/diluted with a little solvent (tap water as a rule). The dilution is to be carried out in this process such that the FO membrane used is not damaged by the still greatly increased electrolyte concentration (no crystallization at the membrane or similar). All the concentrates can be present from the start in the concentrate solution or can only be added to the batch over time.

If the concentrates are only added with a time delay, the osmotic pressure gradient can be maintained in a range ideal for the effectiveness of the FO membrane.

Possibilities for the initial dilution/solution of the concentrates and for priming (filling) the secondary side:

- The filter is prefilled and/or the batch is sufficiently prefilled to start the process and to fill the secondary side/secondary circuit
- Prime (fill) the secondary side/secondary circuit by generating a vacuum→pump sucks in filtrate at the secondary side and fills the batch bag and the secondary side of the filter (monitoring of the transmembrane pressure by a pressure sensor).

Prime (fill) the secondary side/secondary circuit by excess pressure on the primary side→the pressure source on the primary side presses filtrate and fills the batch bag and the secondary side of the filter (monitoring of the transmembrane pressure by a pressure sensor)

Use fluid for priming the filter from the preceding filling process as a priming solution.

It is possible initially only to operate/fill the filtrate side with a minimal, i.e. reduced, circuit→reduced secondary volume (suitable, small bag shape, FO filter with a reduced secondary volume.

Later addition of water e.g. by volume from FO membrane or by manual addition site at the batch Target: Smaller priming volume Preparation of the Solution The concentrated solution is conducted past the secondary side of the FO membrane. The high osmotic pressure gradient between the raw water and the solution produces a continuous filtrate flow over the FO membrane into the batch. With a closed batch, the osmotic pressure gradient and thus the production of permeate decreases over time. A gradient is, however, obtained up to a reaching of an electrolyte concentration typical for a physiological solution (electrolyte concentration approximately 0.15 mol/L in the completed dialyzate).

Stop of Preparation

Rigid-volume system is filled→target volume is reached/ static pressure increases 4 measure pressure or the process stops on its own (p_static=p_osmosis)

Switch-off via conductivity or conductivity only protective system

Switch-off via weight determination

Time controlled

Measure TMP (transmembrane pressure)/measure filtrate flow

The process ends as soon as the mixing ratio of A concentrate to permeate e.g. amounts to 1:35 (=mixing ratio for completed concentrate).

Tank (rigid volume)

Advantages of the present invention in a preferred embodiment are:

An FO process (in particular FO membranes using aquaporin technology) utilizes the osmotic pressure gradient for the filtration of tap water. The energy-intensive production of permeate is "omitted" and dialyzate is prepared directly. Comparatively high filtration rates are nevertheless achieved:

FO filter (e.g. Aquaporin Inside HFFO2): 22.60 liters/m$^2$/hour (25° C./5.8% NaCl solution vs. tap water), RO filter, e.g. 50 liters/m$^2$/hour at 15 bar.

Since the treatment process takes place directly before the use of the fluid, i.e. there is no pipeline network present therebetween, the effort to maintain the required hygiene is simplified. In addition, new possibilities with respect to portability are conceivable due to continuing miniaturization.

In an FO process, the energy-intensive production of filtrate (permeate) is omitted and physiological solution (dialyzate) is prepared directly.

The production of permeate over an FO membrane is technically less intensive in comparison with all said methods (only one FO membrane instead of a plurality of adsorber cartridges, no pipeline systems (adapted for high pressures)) and is therefore suitable for domestic systems such as are typical in PD dialysis.

The total system is thus more space saving and cost saving, less complex, and easier to clean.

In addition, a better filtrate quality can be expected in comparison with adsorber technology since the retention rates of the FO membranes almost reach the retention rates of RO membranes (RO technology currently implements the maximum retention rate of infiltration processes)☐ Important in the preparation of hygienically particularly critical PD solutions that are directly infiltrated into the abdomen of a patient.

Shipping of dry concentrate bags or of highly concentrated concentrates instead of the current ready-to-use liquid solutions (lower transport weight, better shelf life, and sterility)

The technology overall is suitable for a decentralized preparation of physiological and hygienic solutions as required The process is considerably less loud than an RO system with an associated pump to produce pressure→better suited to the domestic environment.

FIG. 2 shows an apparatus for preparing a macrobatch in a schematic view:

Reference numeral 20 shows the water connection, 21 the circulation pump of the mixing circuit, 23 the FO filter, 24 the conductivity-temperature measuring cell for raw water and backflow monitoring (could also be arranged between the container 25 and the circulation pump 21 in the suction line), 25 the container, preferably a bag with concentrate(s), and 22 the drain. As can be seen from FIG. 2, the first part of the apparatus is not designed as a circuit in this embodiment.

The FO filter is preferably disposable/semidisposable and is replaced as required (fixed interval, after a specific volume of filtrate, bubble point test/pressure retention test failed).

There can be named as options/extension possibilities:

Air separation in the circuit to avoid air at the filter

Pressure increase at the raw water side to increase the raw water flow or to superpose an hydrostatic pressure on the FO process (→increase of the filtration rate)

Combination with electrodialysis to increase the (volumetric) concentration of the freely movable electrolytes by applying an electric field→increased concentration of the electrolytes at the filter Introduction of a physiologically neutral substance to increase the osmotic pressure Introduction of a substance (FO agent) separably in a further step—subsequent separation of the agent from the product (as usual today) e.g. via thermal process, filtration, or by separation in the magnetic field (on a use of a ferrofluid as the agent).

Reuse of already consumed dialyzate by supplying the consumed dialyzate at the primary side/bag emptying-→waste weight and volume smaller.

Consumed dialyzate is reused during the entire dialysis

Consumed dialyzate is used at the start of the process (fill secondary circuit)

Monitoring of the transmembrane pressure (thresholds specifically for FO filters) to avoid damage to the FO filter (→important for aquaporin filters)

FO membrane tests to monitor the integrity of the filter

Filling/emptying of a plurality of bags simultaneously

Monitoring of the conductivity in the batch, in the suction line upstream of the FO filter, or downstream of the FO filter to control the filtrate production process Heater and/or heat exchanger in the primary or secondary circuit (preferred) to bring the raw water/filtrate to a temperature ideal for the FO process (25 to 50° C.)

Additional ultrafilter in the feed line upstream of the FO circuit to retain high microbiological, chemical, or physical contaminants and thus to reduce the fouling of the FO filter and to achieve longer shelf lives Additional ultrafilter downstream of the FO circuit to retain still present microbiological (endotoxins), chemical or physical contaminants Test of the FO filter (e.g. measurement of the osmotic pressure) before and after the batch filling to ensure the filter effect and thus the validity of the batch. Release of the batch only after a successful test (e.g.)

In principle analogously all the described embodiments as part of the microbatch approach Possible application areas of the invention are:

Prepare HD solution/batch for a treatment, e.g. 70 L

Prepare PD solution/batch for a treatment or a plurality of bags (e.g. 5 L bags)

Mobile preparation of NaCL solution (after catastrophes, emergencies, or on poor energy supply)

Fill genius tank with FO system, prepare acute bags

FIG. 3 shows an apparatus substantially corresponding to FIG. 1, but with two containers 14 being provided that can be fluidically separated by means of valves V from the second circuit, i.e. from the mixing circuit, or can connected to it. During the preparation of the solution, one container 14 is alternately connected to the circuit and the other container 14 is removed and is used with a dialysis machine, i.e. as part of the treatment.

The invention claimed is:

1. An apparatus for preparing dialyzate, the apparatus comprising a first part and a second part, the first part comprising a primary side of a filter and a water connection or a water container fluidically connected to the primary side of the filter, wherein the filter is capable of preparing purified water from water through forward osmosis and the second part is configured as a circuit and comprises a secondary side of the filter, a reservoir, a filtrate line that leads from the secondary side of the filter to the reservoir, and a supply line leading from the reservoir to the secondary side of the filter, with the reservoir being at least one collection container configured to fluidically connect to a dialysis machine.

2. The apparatus in accordance with claim 1, wherein the at least one collection container is a bag that is designed with flexible walls overall or in part or is a cartridge that is designed with rigid walls overall or in part.

3. The apparatus in accordance with claim 1, wherein the first part of the apparatus is also designed as a circuit, wherein the first part comprises the water container and further comprises a backflow line running from the filter to the water container.

4. The apparatus in accordance with claim 1, wherein dialysis concentrate is located in the at least one collection container.

5. The apparatus in accordance with claim 1, wherein the at least one collection container is a plurality of collection containers and a valve arrangement is present that is configured to alternately connect a respective collection container of the plurality of collection containers in fluid communication with the second part of the apparatus.

6. The apparatus in accordance with claim 1, further comprising a connector, a tube, or a connector for a tube that fluidically connects the at least one collection container to the dialysis machine.

7. The apparatus in accordance with claim 1, wherein a bicarbonate concentrate and/or an acid concentrate is present in the at least one collection container for the preparation of dialyzate.

8. The apparatus in accordance with claim 1, wherein a plurality of compartments are provided in the at least one collection container in which one or more concentrates are present.

9. The apparatus in accordance with claim 1, wherein concentrate is present in the at least one collection container as a powder, a granulate, a slurry, or in liquid form.

10. The apparatus in accordance with claim 1, wherein one or more pumps are provided in the first part of the apparatus and/or in the second part of the apparatus.

11. The apparatus in accordance with claim 1, wherein one or more conductivity measuring cells are provided in the first part of the apparatus and/or in the second part of the apparatus.

12. The apparatus in accordance with claim 1, further comprising a concentrate line that is connected to a further reservoir containing a dialysis concentrate, which opens into the second part of the apparatus.

13. A method of preparing dialyzate using the apparatus in accordance with claim 1, comprising: supplying water to the primary side of the filter resulting in permeate being supplied to the secondary side by forward osmosis; and supplying a dialysis concentrate or a dialysis concentrate premixed with the permeate to the secondary side of the filter from the at least one collection container and/or from another source.

14. The method in accordance with claim 13, wherein the dialyzate or the dialysis concentrate is conveyed in the circuit on the secondary side of the filter until the conductivity and/or a concentration or another parameter representative for these parameters corresponds to a desired value or is in a desired value range.

15. The method in accordance with claim 13, wherein the at least one collection container is a plurality of collection containers present in the second part of the apparatus, the method further comprising supplying the dialyzate or the dialysis concentrate to the second part from one collection container of the plurality of collection containers and supplying a prepared dialyzate to a dialysis machine from another collection container of the plurality of collection containers.

16. The method in accordance with claim 13, wherein a physiologically compatible substance or a substance to be separated prior to the use as a prepared dialyzate are added to increase the osmotic pressure on the secondary side of the filter.

* * * * *